(12) United States Patent
Shih et al.

(10) Patent No.: US 10,307,530 B2
(45) Date of Patent: Jun. 4, 2019

(54) PRESSURE SENSING IN IMPLANTABLE DRUG PUMPS

(71) Applicants: Jason Shih, Yorba Linda, CA (US); Andrew Dunn, Santa Monica, CA (US)

(72) Inventors: Jason Shih, Yorba Linda, CA (US); Andrew Dunn, Santa Monica, CA (US)

(73) Assignee: MINIPUMPS, LLC, Pasadena, CA (US)

(*) Notice: Subject to any disclaimer, the term of this patent is extended or adjusted under 35 U.S.C. 154(b) by 653 days.

(21) Appl. No.: 14/982,246

(22) Filed: Dec. 29, 2015

(65) Prior Publication Data

US 2016/0184516 A1    Jun. 30, 2016

Related U.S. Application Data

(60) Provisional application No. 62/098,758, filed on Dec. 31, 2014.

(51) Int. Cl.
| | |
|---|---|
| *A61M 5/142* | (2006.01) |
| *A61M 5/145* | (2006.01) |
| *G01L 1/22* | (2006.01) |

(52) U.S. Cl.
CPC .... *A61M 5/14276* (2013.01); *A61M 5/14593* (2013.01); *A61M 2005/14204* (2013.01);
(Continued)

(58) Field of Classification Search
CPC ......... G01L 1/22; G01L 1/2287; G01L 1/225; G01L 27/00; A61M 5/14276;
(Continued)

(56) References Cited

U.S. PATENT DOCUMENTS

| | | | | |
|---|---|---|---|---|
| 5,026,255 A | * | 6/1991 | Carpenter | F04B 11/0058 137/625.4 |
| 2009/0306595 A1 | * | 12/2009 | Shih | A61M 5/14276 604/151 |

(Continued)

FOREIGN PATENT DOCUMENTS

| | | |
|---|---|---|
| WO | 00/53243 A1 | 9/2000 |
| WO | 2012/116038 A2 | 8/2012 |

OTHER PUBLICATIONS

International Search Report and Written Opinion issued in a corresponding International Application No. PCT/US2015/067798 dated Apr. 14, 2016.

*Primary Examiner* — Bradley J Osinski
*Assistant Examiner* — Nilay J Shah
(74) *Attorney, Agent, or Firm* — Morgan, Lewis & Bockius LLP

(57) ABSTRACT

In various embodiments, approaches to calibrating an implantable drug-delivery device feature a drug reservoir, an expandable electrolysis chamber, and an integrated strain gauge using a refill apparatus having one or more pumps, one or more refill reservoirs, an outlet fluid channel fluidically connected to the refill reservoir(s), and a needle having a lumen in fluid communication with the outlet fluid channel include inserting a needle into a refill port of the implantable drug-delivery device, monitoring a pressure change within the device, monitoring a pressure level of one or more components of the implantable drug-delivery device, and calibrating the monitored pressure level of the component(s) of the implantable drug-delivery device to the monitored pressure level of the outlet fluid channel.

13 Claims, 12 Drawing Sheets

(52) U.S. Cl.
CPC ............ *A61M 2005/14513* (2013.01); *A61M 2205/702* (2013.01); *A61M 2209/045* (2013.01); *G01L 1/22* (2013.01); *G01L 1/225* (2013.01); *G01L 1/2287* (2013.01)

(58) Field of Classification Search
CPC ............ A61M 5/145; A61M 5/14586; A61M 5/14593; A61M 2005/14513; A61M 2005/14204
See application file for complete search history.

(56) References Cited

U.S. PATENT DOCUMENTS

| | | |
|---|---|---|
| 2010/0087778 A1 | 4/2010 | Genosar et al. |
| 2011/0275987 A1 | 11/2011 | Caffey et al. |
| 2013/0204202 A1 | 8/2013 | Trombly et al. |

\* cited by examiner

DETACHABLE
31 Ga NEEDLE

PRESSURE SENSING IN IMPLANTABLE DRUG PUMPS

RELATED APPLICATION

This application claims the benefit of and priority to U.S. Provisional Patent Application No. 62/098,758, filed Dec. 31, 2014, the entire disclosure of which is hereby incorporated herein by reference.

TECHNICAL FIELD

In various embodiments, the present invention relates generally to implantable pumps for drug administration, featuring pressure sensors for, e.g., refill and/or safety monitoring.

BACKGROUND

Medical treatment often requires the administration of a therapeutic agent (e.g., medicament, drugs, etc.) to a particular part of a patient's body. As patients live longer and are diagnosed with chronic and/or debilitating ailments, the need to place even more protein therapeutics, small-molecule drugs, and other medications into targeted anatomical areas will only increase. Some maladies, however, are difficult to treat with currently available therapies and/or require administration of drugs to difficult-to-reach anatomical regions. Many of these therapies would benefit from concentrated target-area treatment, which would reduce systemic side effects. Furthermore, certain drugs such as protein therapeutics are expensive, costing thousands of dollar per vial. For these reasons, new and improved approaches to targeted drug delivery are constantly sought.

Implantable drug-delivery devices with refillable drug reservoirs address and overcome many of the problems associated with conventional drug-delivery modalities. They generally facilitate controlled delivery of pharmaceutical solutions to a specified target. As the contents of the drug reservoir deplete, a clinician may refill the reservoir in situ, i.e., while leaving the device implanted within the patient's body.

Monitoring and controlling the administration of pharmaceuticals can be critically important, particularly when implanted drug pump are utilized, as such devices may often not be constantly closely monitored. Thus, implantable drug pumps would benefit from autonomous safeguards sufficient to ensure proper dosing and performance monitoring. Furthermore, the drug reservoirs of implantable pumps are likely to be of limited size and their contents would ideally be monitored to ensure timely refilling or replacement.

Accordingly, there is a need for implantable pumps that incorporate sensors for monitoring various parameters related to pump performance and drug administration.

SUMMARY

In various embodiments, the present invention relates to implantable drug pumps that incorporate pressure sensing systems in any of a variety of different components and configurations. For example, pressure sensors may be embedded within different structural components (e.g., drug reservoirs, fluidic pathways, and/or electrolysis chambers) to measure and monitor various pressures within the drug delivery system throughout the implant's life.

In an aspect, embodiments of the invention feature an implantable drug-delivery device that includes or consists essentially of a housing having an interior, a cannula, a refill port, circuitry, and, disposed within the interior of the housing, (i) a flexible drug reservoir for containing a therapeutic agent therein, (ii) an expandable electrolysis chamber, (iii) a diaphragm separating the electrolysis chamber from the drug reservoir, and (iv) a strain gauge integrated with the flexible membrane. The flexible drug reservoir includes or consists essentially of a flexible membrane. The electrolysis chamber contains therewithin a plurality of electrolysis electrodes and an electrolysis fluid. The cannula is fluidically coupled to the drug reservoir and has an exit port outside the housing. The refill port is fluidically coupled to the drug reservoir and has an entry port outside the housing. The circuitry operates the electrodes to cause evolution of gas from the electrolysis fluid to thereby expand the electrolysis chamber and drive therapeutic agent from the drug reservoir out through the cannula. The circuitry also monitors pressure changes within the drug reservoir detected by the strain gauge.

Embodiments of the invention may include one or more of the following in any of a variety of combinations. At least a portion of the circuitry may be disposed within the interior of the housing. The circuitry may include a quarter-bridge strain gauge circuit. The diaphragm may be flexible and/or corrugated. The flexible membrane may include a region of maximum deformation as a function of fill volume of the drug reservoir. At least a portion of the strain gauge may be disposed along or across the region of maximum deformation. The at least a portion of the strain gauge may be configured to trigger an open circuit therewithin when a pressure within the drug reservoir exceeds a threshold pressure. The at least a portion of the strain gauge may include or consist essentially of two interlocking portions configured to reversibly separate from each other when the pressure within the drug reservoir exceeds the threshold pressure. The strain gauge may be integrated with the flexible membrane in a sinuous or spiral configuration.

In another aspect, embodiments of the invention feature an implantable drug-delivery device that includes or consists essentially of a housing having an interior, a cannula, a refill port, circuitry, and, disposed within the interior of the housing, (i) a drug reservoir for containing a therapeutic agent therein, (ii) a substrate, (iii) an expandable electrolysis chamber, (iv) a diaphragm separating the electrolysis chamber from the drug reservoir, and (v) a strain gauge integrated with the substrate. The expandable electrolysis chamber contains therewithin a plurality of electrolysis electrodes and an electrolysis fluid. The electrodes are disposed on, over, or in the substrate. The cannula is fluidically coupled to the drug reservoir and has an exit port outside the housing. The refill port is fluidically coupled to the drug reservoir and has an entry port outside the housing. The circuitry operates the electrodes to cause evolution of gas from the electrolysis fluid to thereby expand the electrolysis chamber and drive therapeutic agent from the drug reservoir out through the cannula. The circuitry also monitors pressure changes within the electrolysis chamber detected by the strain gauge.

Embodiments of the invention may include one or more of the following in any of a variety of combinations. At least a portion of the circuitry may be disposed within the interior of the housing. The circuitry may include a quarter-bridge strain gauge circuit. The diaphragm may be flexible and/or corrugated. The strain gauge may be disposed in a center region of the substrate. The electrodes may be disposed in a peripheral region of the substrate at least partially surrounding the center region. The substrate may include a buffer region disposed between the center region and the peripheral region, and the buffer region may be free of electrodes and the strain gauge.

In yet another aspect, embodiments of the invention feature an implantable drug-delivery device that includes or consists essentially of a housing having an interior, a cannula, a refill port, circuitry, a tubular component, a strain gauge, and, disposed within the interior of the housing, (i) a drug reservoir for containing a therapeutic agent therein, (ii) an expandable electrolysis chamber containing therewithin a plurality of electrolysis electrodes and an electrolysis fluid, and (iii) a diaphragm separating the electrolysis chamber from the drug reservoir. At least a portion of the tubular component and/or at least a portion of the circuitry may be disposed within the interior of the housing. The cannula is fluidically coupled to the drug reservoir and has an exit port outside the housing. The refill port is fluidically coupled to the drug reservoir and has an entry port outside the housing. The tubular component corresponds to one or more of a portion of the cannula, a tube fluidically coupled to the cannula, a check valve fluidically coupled to the cannula, a tube fluidically coupled to the drug reservoir, or a portion of the refill port. The strain gauge is integrated with the tubular component. The circuitry operates the electrodes to cause evolution of gas from the electrolysis fluid to thereby expand the electrolysis chamber and drive therapeutic agent from the drug reservoir out through the cannula. The circuitry also monitors pressure changes within the tubular component detected by the strain gauge. The circuitry may include a quarter-bridge strain gauge circuit. The diaphragm may be flexible and/or corrugated. The strain gauge may be integrated with the tubular component in a helical configuration.

In another aspect, embodiments of the invention feature a method of calibrating an implantable drug-delivery device. A refill apparatus is provided. The refill apparatus includes or consists essentially of at least one pump, at least one reservoir, an outlet fluid channel fluidically connected to the at least one reservoir, and a needle having a lumen in fluid communication with the outlet fluid channel. The needle is inserted into a refill port of the implantable drug-delivery device. A pressure level of the outlet fluid channel is monitored. A pressure level of at least one component of the implantable drug-delivery device is monitored. The monitored pressure level of the at least one component of the implantable drug-delivery device is calibrated to the monitored pressure level of the outlet fluid channel. The calibrated pressure level of the at least one component of the implantable drug-delivery device is stored within the implantable drug-delivery device.

Embodiments of the invention may include one or more of the following in any of a variety of combinations. An error condition may be reported if the monitored pressure level of the outlet fluid channel and/or the monitored pressure level of the at least one component of the implantable drug-delivery device deviates from a predetermined range of pressures (e.g., exceeds a predetermined threshold maximum pressure and/or falls below a predetermined threshold minimum pressure). A pressure level of at least one additional component of the implantable drug-delivery device may be monitored. The monitored pressure level of the at least one additional component of the implantable drug-delivery device may be calibrated to the monitored pressure level of the at least one component of the implantable drug-delivery device. The at least one component of the implantable drug-delivery device may include, consist essentially of, or consist of a drug reservoir for containing a therapeutic agent therein (e.g., a flexible reservoir), an expandable electrolysis chamber comprising therewithin a plurality of electrolysis electrodes and an electrolysis fluid, at least a portion of a cannula, a tube fluidically coupled to the cannula, a check valve fluidically coupled to the cannula, a tube fluidically coupled to the drug reservoir, and/or a portion of the refill port. After the needle is inserted into the refill port of the implantable drug-delivery device, at least one of the pumps may be actuated to introduce therapeutic agent from at least one of the reservoirs of the refill apparatus into the drug reservoir, introduce a rinsing fluid from at least one of the reservoirs of the refill apparatus into the drug reservoir, remove therapeutic agent from the drug reservoir, and/or remove rinsing fluid from the drug reservoir.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and may exist in various combinations and permutations. As used herein, the terms "approximately" and "substantially" mean ±10%, and in some embodiments, ±5%. The term "consists essentially of" means excluding other materials that contribute to function, unless otherwise defined herein. Nonetheless, such other materials may be present, collectively or individually, in trace amounts.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Embodiments of the present invention relate, generally, to implantable drug pump devices with refillable drug reservoirs. Various embodiments described herein relate specifically to drug pump devices implanted into the eye (e.g., between the sclera and conjunctiva); however, many features relevant to such ophthalmic pumps are also applicable to other drug pump devices, such as, e.g., implantable insulin pumps, inner ear pumps, and brain pumps.

Figure 1:
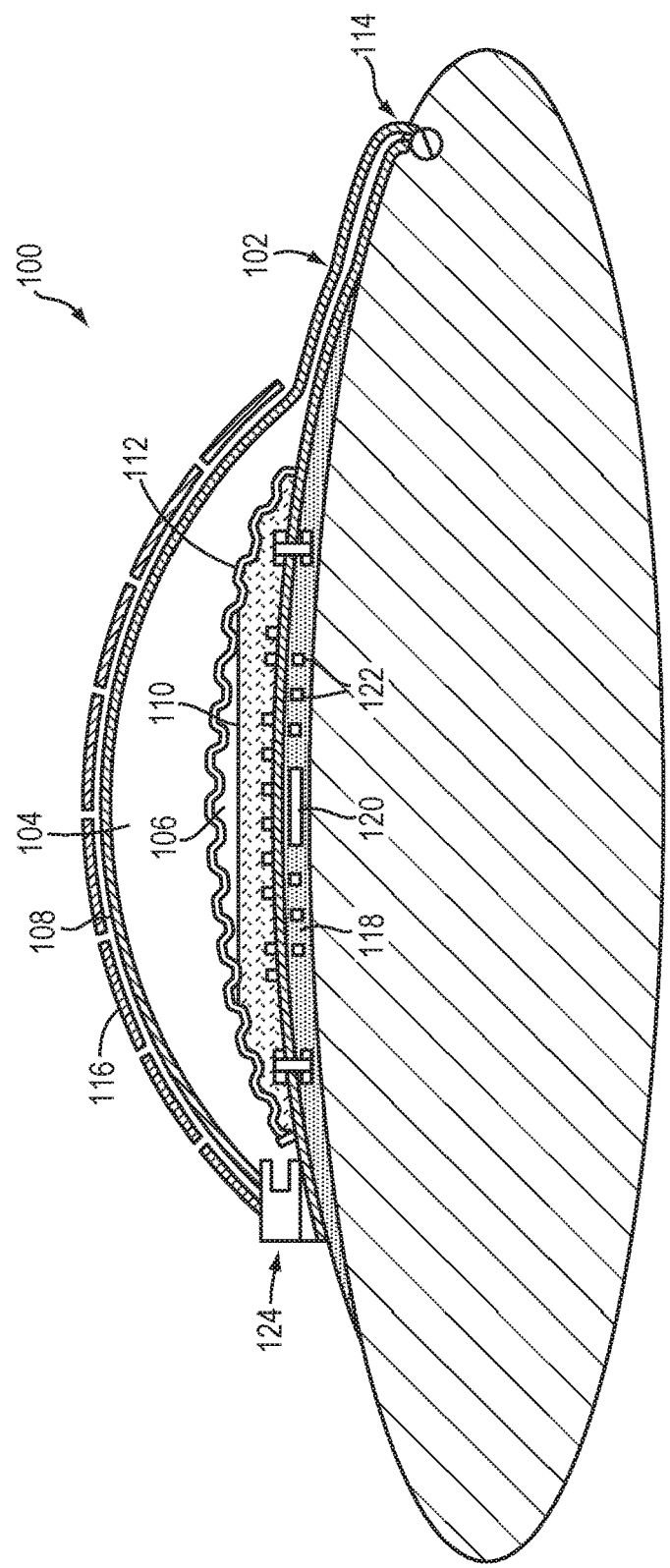
FIG. 1 is a side view of an implantable, refillable drug pump device in accordance with various embodiments of the invention.

FIG. 1 illustrates an exemplary electrolytically driven drug pump device 100 in accordance herewith (aspects of which are described in detail in U.S. application Ser. Nos. 12/463,251 and 13/632,644, the entire disclosures of which are hereby incorporated by reference). The drug pump device 100 includes a cannula 102 and a pair of chambers 104, 106 bounded by a flexible envelope 108. The top chamber 104 defines a drug reservoir that contains the drug to be administered in liquid form, and the bottom chamber 106 contains a liquid which, when subjected to electrolysis using electrolysis electrodes 110, evolves a gaseous product. The electrolyte liquid contained within the bottom chamber 106 may include, consist essentially of, or consist of, for example, a saline (i.e., NaCl and $H_2O$) solution, a solution that contains either magnesium sulfate or sodium sulfate, pure water, or any non-toxic solution. The two chambers 104, 106 are separated by a diaphragm 112. The diaphragm 112 may be elastic and/or may be corrugated to provide for expansion thereof in response to the phase-change of the fluid within the bottom chamber 106 from a liquid to a gaseous state. The diaphragm 112 may be manufactured from, for example, one or more parylene films and/or a composite material.

The cannula 102 connects the top drug chamber 104 with a check valve 114 inserted at the site of administration or anywhere along the fluid path between the drug reservoir and site of administration. The envelope 108 resides within a shaped protective shell 116 made of a flexible material (e.g., a bladder or collapsible chamber) or a relatively rigid biocompatible material (e.g., medical-grade polypropylene). Control circuitry 118, a battery 120, and an induction coil 122 for power and data transmission are embedded between the bottom wall of the electrolyte chamber 106 and the floor of the shell 116. Depending on the complexity of the control functionality it provides, the control circuitry 118 may be implemented, e.g., in the form of analog circuits, digital integrated circuits (such as, e.g., microcontrollers), or programmable logic devices. In some embodiments, the control circuitry 118 includes a microprocessor and associated memory for implementing complex drug-delivery protocols. The drug pump device 100 may also include various sensors (e.g., pressure and flow sensors) for monitoring the status and operation of the various device components, and such data may be logged in the memory for subsequent retrieval and review.

In various embodiments, the induction coil 122 permits wireless (e.g., radio-frequency (RF)) communication with an external controller (e.g., a portable control handset), which may also be used, for example, to charge the battery 120. The coil 122 may be or resemble, for example, a coil described in U.S. patent application Ser. No. 13/491,741, filed on Jun. 8, 2012, the entire disclosure of which is incorporated by reference herein. The external controller may be used to send wireless signals to the control circuitry 118 in order to program, reprogram, operate, calibrate, or otherwise configure the operation of the pump 100. The control circuitry 118 may, for example, communicate electrically with the electrolysis electrodes 110 by means of metal interconnects extending thereto.

Importantly for the prolonged use of the drug pump device 100 following implantation, the device 100 includes one or more refill ports 124 in fluid communication at least with the flexible reservoir 104, which permit a refill needle (not shown) to be inserted therethrough. Each refill port 124 may have a venting arrangement integrated therewith for, e.g., the venting of excess gas and/or pressure equalization, as described in U.S. patent application Ser. No. 14/317,848, filed Jun. 27, 2014, or U.S. patent application Ser. No. 14/807,940, filed Jul. 24, 2015, the entire disclosure of each of which is hereby incorporated by reference herein.

Implantable, refillable drug pump devices need not, of course, have the particular configuration depicted in FIG. 1. Various modifications are possible, including, e.g., devices in which the drug reservoir and pump chamber are arranged side-by-side (rather than one above the other), and/or in which pressure generated in the pump chamber is exerted on the drug reservoir via a piston (rather than by a flexible diaphragm). Furthermore, the pump need not in all embodiments be driven electrolytically, but may exploit, e.g., osmotic or electroosmotic drive mechanisms, or even pressure generated manually.

Figure 2:
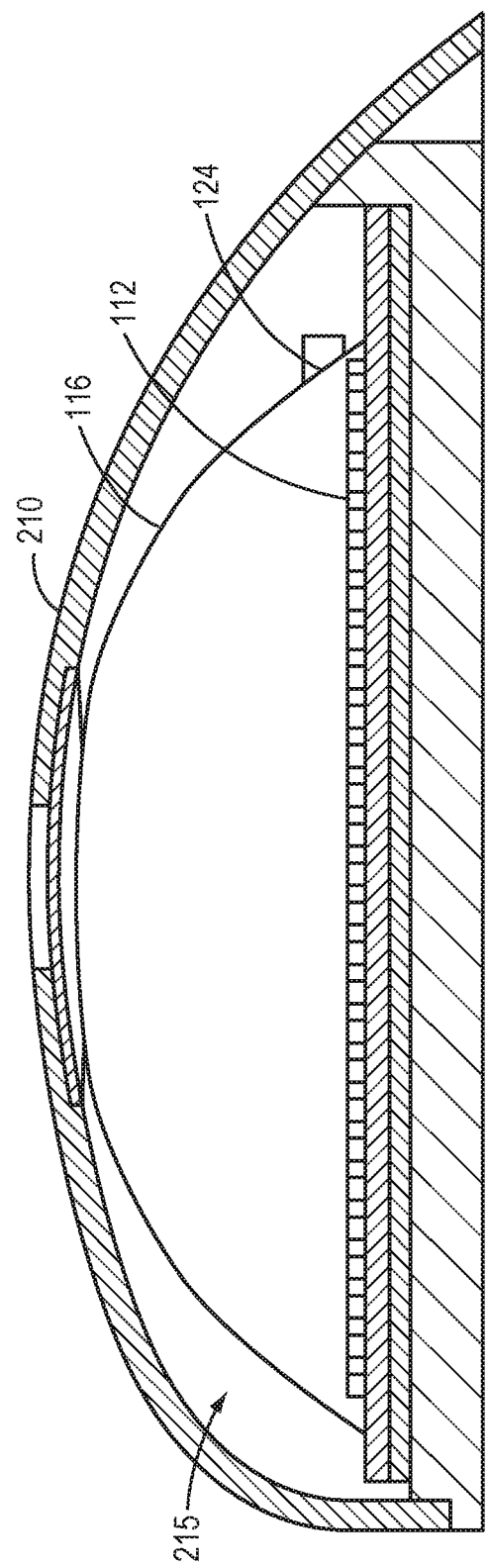
FIG. 2 is a side view of the device shown in FIG. 1 deployed within an exterior housing in accordance with various embodiments of the invention.

The components illustrated in FIG. 1 may be deployed within a hard outer shell 210, as shown in FIG. 2. The shell 210 may be made of, for example, titanium. The inner shell 116 lies within a second envelope formed by the outer shell 210, creating an enclosed region 215 between the shells 116, 210.

Figure 3:
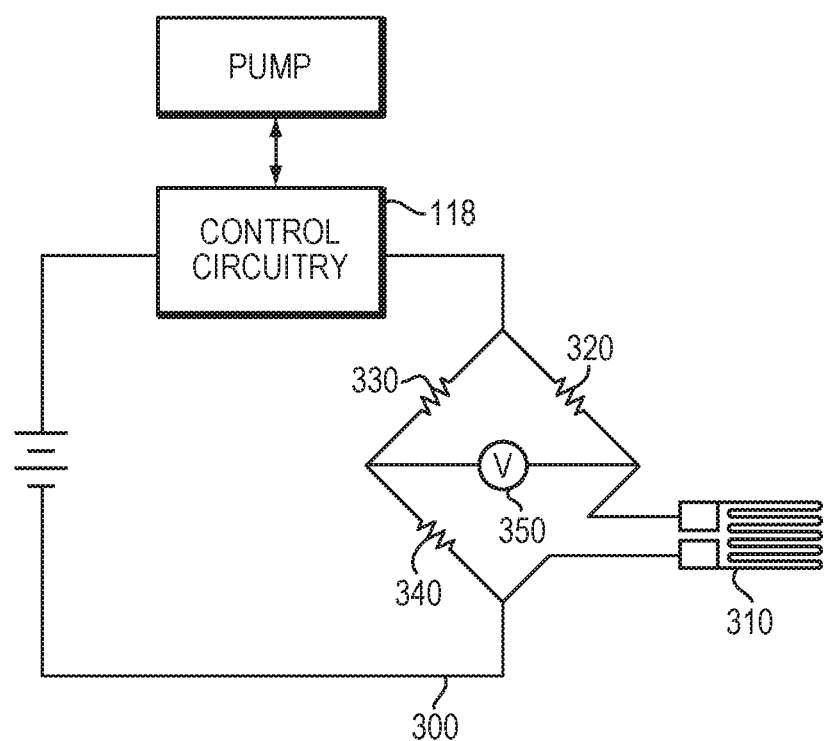
FIG. 3 is a schematic circuit diagram of a quarter-bridge strain-sensing circuit in accordance with various embodiments of the invention.

Drug pump devices in accordance with embodiments of the present invention advantageously incorporate pressure sensors in one or more components for, e.g., safety or performance monitoring. FIG. 3 schematically depicts an exemplary quarter-bridge strain gauge circuit 300 that may be utilized to monitor changes in pressure within a drug pump device. The circuit 300 includes a strain gauge 310 that may include or consist essentially of a foil or wire embedded within or affixed to a surface of a drug-pump component. As known in the art, positive or negative pressure applied to the component will tensilely or compressively strain the wire of the strain gauge, altering its electrical resistivity. Circuits such as circuit 300 may be utilized to measure such differences and correlate them to pressure changes within the device. Typically, a rheostat resistor 320 (which may be variable for, e.g., calibration purposes) of the circuit has a resistance equal to the resistance of strain gauge 310 with no force applied, and two ratio resistors 330, 340 of the circuit 300 have equal resistances. Thus, with no force applied to the strain gauge 310, the "bridge" will be symmetrically balanced and a voltmeter 350 will indicate zero potential difference, representing a lack of force on the strain gauge 310. As the strain gauge 310 is either compressed or tensed via pressure differences within the drug-pump device, its resistance will decrease or increase, respectively, thus unbalancing the bridge and producing an indication at the voltmeter 350. The resulting measurements may be measured, monitored, and recorded within memory, and the measurements may be used to correlate drug-delivery progression (i.e., actuation mechanism movement, opening of check valves, fluid flow through fluidic pathways, volume of drug delivered, etc.). For drug pump devices featuring electrolytic actuation mechanisms (as detailed above), pressure generation may be monitored to control flow rate and detect over-pressurization of the drug reservoir or failures of fluidic pathways. Other strain gauge circuit configurations known in the art may be utilized in embodiments of the present invention, in accordance with circuitry limitations, power constraints, and desired accuracy and sensitivity of the device and the region in which pressure is to be measured.

As shown in FIG. 3, strain gauge circuit 300 may interface with, or even be a portion of, control circuitry 118, and signals from circuit 300 may be utilized during operation of drug pump device 100 for a variety of useful purposes. Strain indications (corresponding to internal pressure changes) may be utilized instead of or in tandem with flow-rates measured by flow sensors disposed within the drug pump device 100 (e.g., proximate or within cannula 102, proximate or within drug reservoir 104, proximate or within refill port 124, etc.) For example, strain measurements from circuit 300 may be utilized to trigger a warning indication in the event of improper operation (e.g., administration of a dose of therapeutic agent exceeding a pre-defined or user-defined maximum dosage, refilling drug reservoir 104 with a volume of therapeutic agent exceeding a pre-defined or user-defined maximum refill amount, lack of or slow flow of therapeutic agent from the drug reservoir 104 during dose administration, etc.). Strain measurements from circuit 300 may be utilized to monitor and/or meter dosing of the therapeutic agent, as the volume of the dispensed therapeutic agent may be calculated based on the strain measurements via, e.g., control circuitry 118. Strain measurements from circuit 300 may even be utilized to monitor operational performance of drug pump device 100 over time. For example, the amount of pressure generated and/or the amount of time required to do so within the pump chamber 106 may vary as a function of time due to, e.g., condition of the electrolysis electrodes and/or the electrolysis fluid. The operation of the pump chamber 106 may be adjusted by, e.g., control circuitry 118, to maintain constant dosing over time.

Figure 4A:
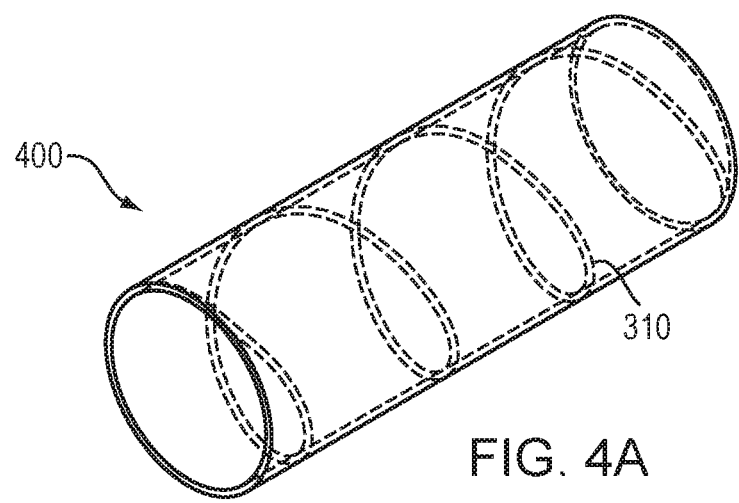
FIG. 4A is a perspective view of a tubular component of a drug pump device incorporating a strain gauge in accordance with various embodiments of the invention.
Figure 4B:
FIG. 4B is a cross-sectional view of the component of FIG. 4A.

FIGS. 4A and 4B depict a portion of a tubular valve component 400 having strain gauge 310 integrated therewith. (As utilized herein, a strain gauge being "integrated with" a component of a drug pump device means that the strain gauge is embedded within or disposed on the interior or exterior surface of the component.) The component 400 may be flexible and/or may include, consist essentially of, or consist of a biocompatible material such as parylene. As shown, the strain gauge 310 may be embedded within or disposed on the interior or exterior surface of component 400 in, e.g., a helical configuration. As detailed above, changes in pressure within component 400 may be detected and electrically measured due to concomitant changes in the resistance of strain gauge 310. The component 400 may be a component connecting to, or may even be a portion of, various components of pump device 100, e.g., cannula 102, refill port 124, reservoir 104, check valve 114, etc. Although various ones of the figures depict the strain gauge as being or including a wire, in various embodiments, the wire may be supplemented with or replaced by a film or foil of, e.g., a piezoelectric material.

Figure 5A:
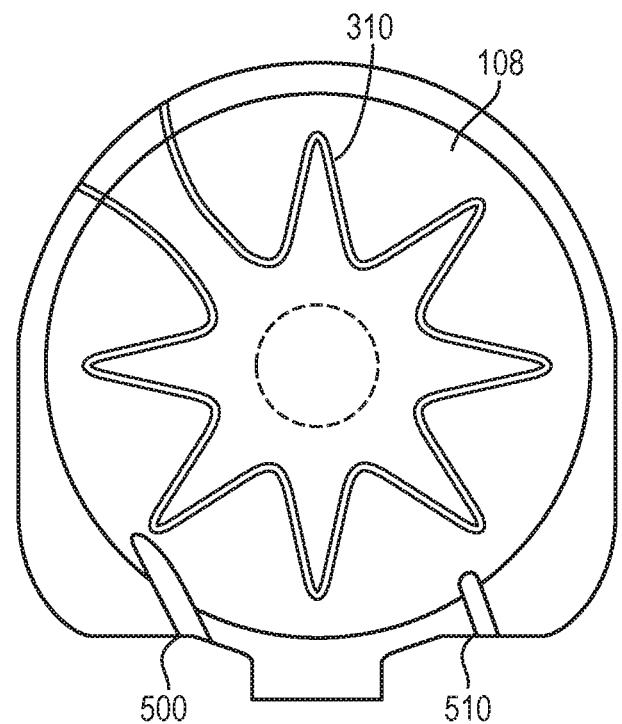
FIG. 5A is a plan view of a portion of a flexible drug reservoir incorporating a strain gauge in accordance with various embodiments of the invention.
Figure 5B:
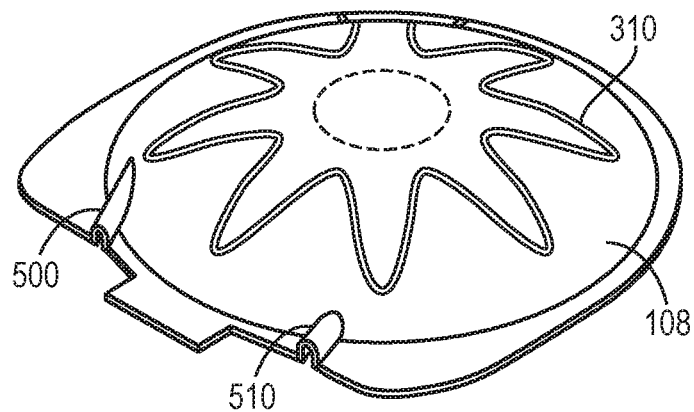
FIG. 5B is a perspective view of the reservoir portion of FIG. 5A.

Embodiments of the present invention also feature pressure-sensing capabilities integrated within the flexible drug reservoir 104 of the pump device 100. FIGS. 5A and 5B depict an exemplary flexible envelope 108 that, at least in part, defines the drug reservoir 104. The envelope 108 may also incorporate, or have disposed thereon, an outlet tube 500 that connects to, or is a portion of, the cannula 102. The envelope 108 may also incorporate, or have disposed thereon, an inlet tube 510 that connects to, or is a portion of, the refill port 124. As shown, the strain gauge 310 may be embedded within or disposed on the interior or exterior surface of envelope 108 in, e.g., a sinuous, star-shaped, or wave-like configuration. As detailed above, changes in pressure within envelope 108 may be detected and electrically measured due to concomitant changes in the resistance of strain gauge 310. In this manner, the residual volume of the liquid within the reservoir 104 may be measured using strain gauge 310. Such measurements may be utilized in conjunction with pump device 100 for, e.g., monitoring the volume of the drug within reservoir 104 during refilling and/or to ensure sufficient drug remains within reservoir 104 for subsequent doses.

Figure 6A:
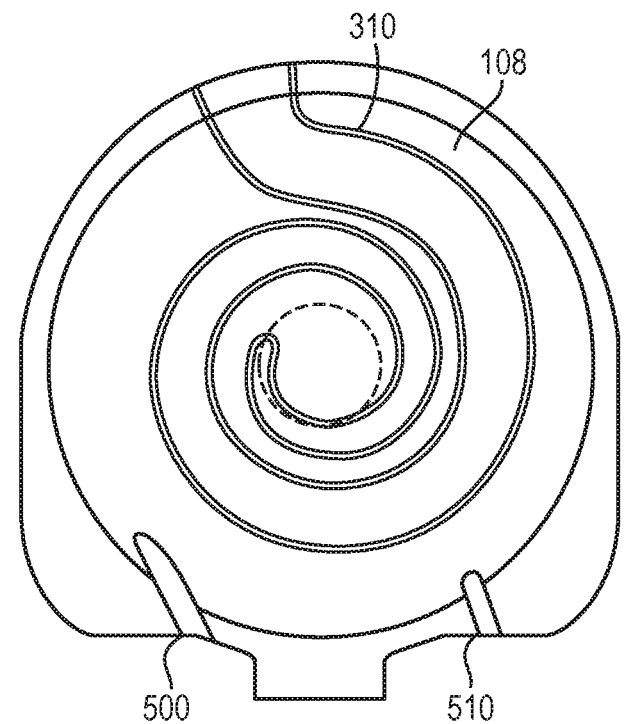
FIG. 6A is a plan view of a portion of a flexible drug reservoir incorporating a strain gauge in accordance with various embodiments of the invention.
Figure 6B:
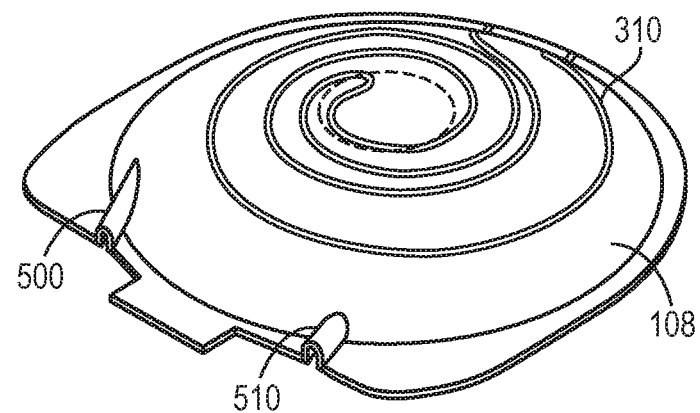
FIG. 6B is a perspective view of the reservoir portion of FIG. 6A.

Similarly, FIGS. 6A and 6B depict an exemplary embodiment of the invention in which strain gauge 310 is embedded within or disposed on the interior or exterior surface of envelope 108 in a spiral configuration. In various embodiments, the spiral configuration of FIGS. 6A and 6B with redundant coiling may have increased sensitivity to changes in the shape of envelope 108 and thus to pressure changes therewithin when compared to various other configurations of strain gauge 310.

Figure 7A:
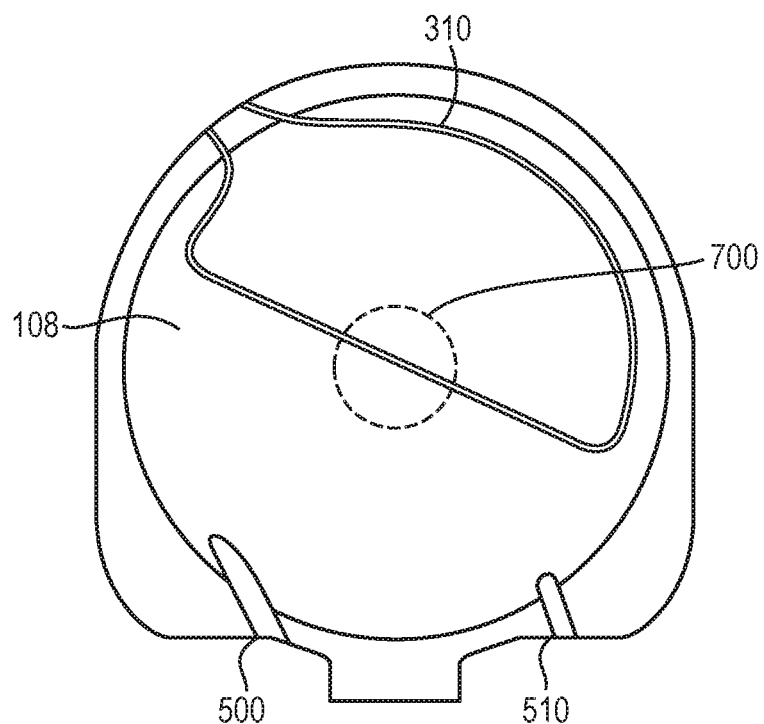
FIG. 7A is a plan view of a portion of a flexible drug reservoir incorporating a strain gauge in accordance with various embodiments of the invention.
Figure 7B:
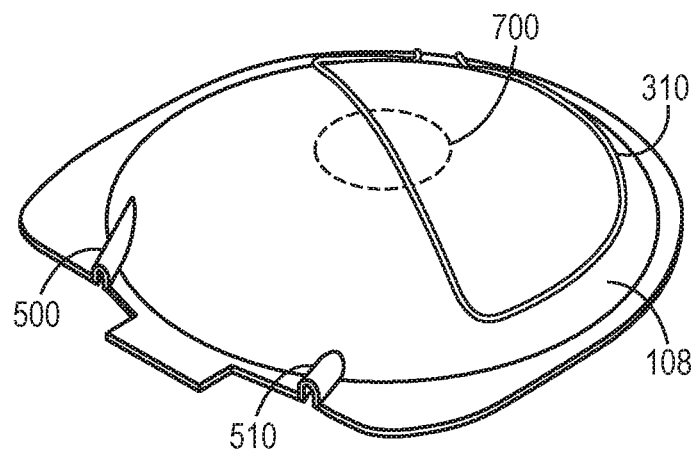
FIG. 7B is a perspective view of the reservoir portion of FIG. 7A.
Figure 7C:
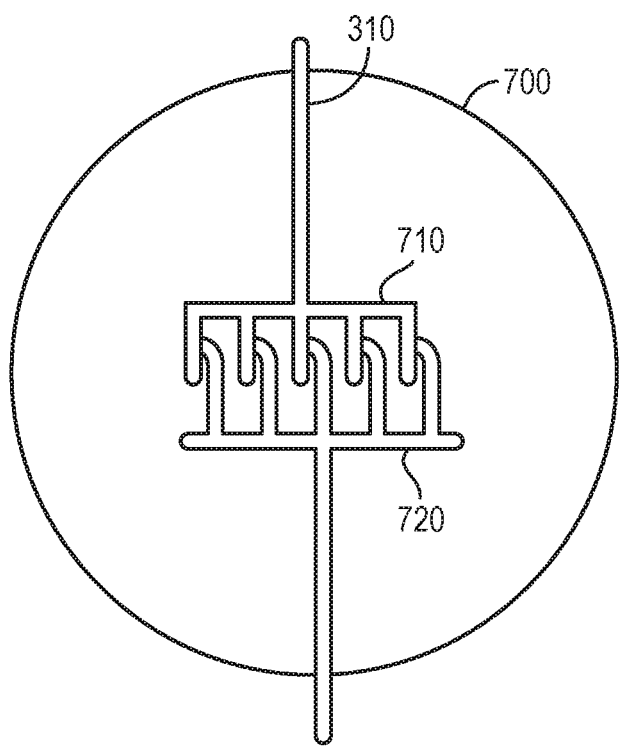
FIG. 7C is an enlarged view of a portion of a flexible drug reservoir incorporating a strain gauge in accordance with various embodiments of the invention.

FIGS. 7A and 7B depict another exemplary embodiment of the invention in which strain gauge 310 is embedded within or disposed on the interior or exterior surface of envelope 108. As shown, the strain gauge 310 extends across or within a region 700 of maximum deformation of the flexible envelope 108. In such embodiments, the strain gauge 310 may also function as a "pressure fuse" if the pressure within reservoir 104 (and thus the deflection of region 700) reaches a maximum threshold pressure. In such cases, the pressure signaled by the strain gauge 310 may signal the pump device to shut down, end an electrolysis cycle, or end a refilling cycle. In various embodiments, the portion of the strain gauge 310 within region 700 may be configured to break or otherwise create an open circuit upon deflection of region 700 at the threshold maximum pressure. In such embodiments, the strain gauge 310 may be electrically in series with the electrolysis circuitry, and thus the strain gauge 310 may disable the pumping chamber 106 if the threshold pressure is reached without the need for software-based intervention. The strain gauge 310 within region 700 may be configured to permanently break when the maximum threshold pressure is reached. In other embodiments, as shown in FIG. 7C, the portion of the strain gauge 310 within region 700 may feature interlocking combs 710, 720 that permit closed-circuit operation of strain gauge 310 during normal operating pressures but separate at pressures exceeding the threshold pressure, creating a reversible open circuit.

Figure 8:
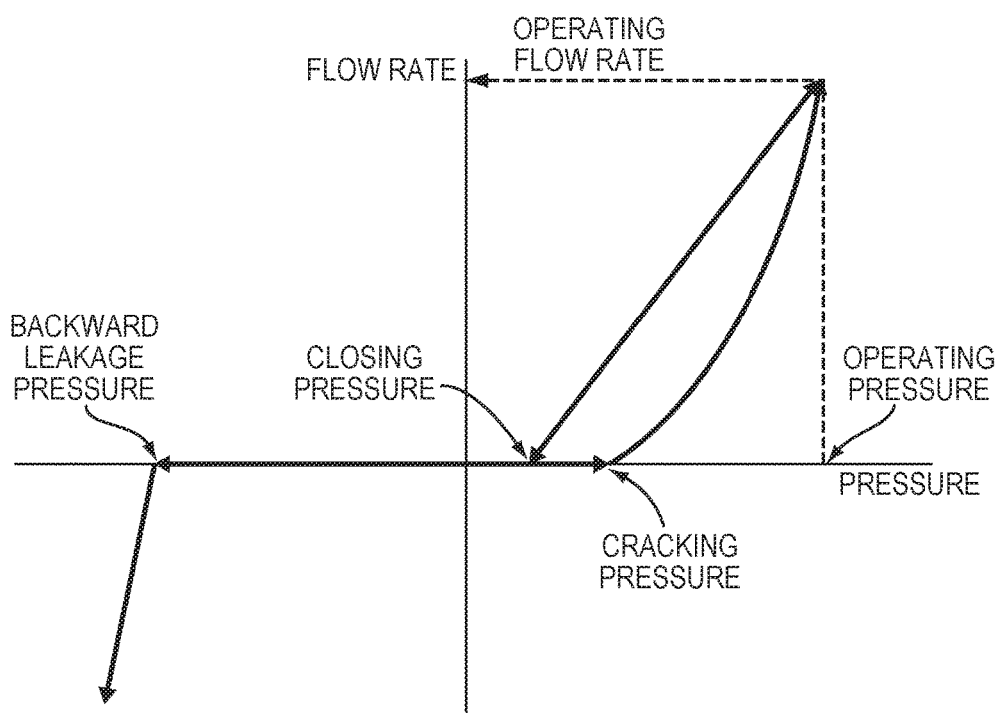
FIG. 8 is a grain of flow rate vs. pressure for an exemplary check valve within a flexible membrane in accordance with various embodiments of the invention.

The strain gauge 310 may also be incorporated into a portion of the drug pump device 100 proximate a check valve (e.g., check valve 114) or in the valve seat thereof to monitor pressure changes signifying opening and/or closing of the valve. As shown in FIG. 8, as pressure on the valve increases, the flexible membrane proximate the valve may expand an appreciable amount before the valve actually opens (i.e., when the cracking pressure is achieved). And, as the pressure on the valve decreases, the flexible valve membrane may gradually return to its original shape until the valve closes when the closing pressure is attained. Such pressure changes may also be detectable proximate other components of drug delivery devices in accordance with embodiments of the invention, e.g., flow sensors proximate or within cannula 102 or elsewhere in the device.

Figure 9:
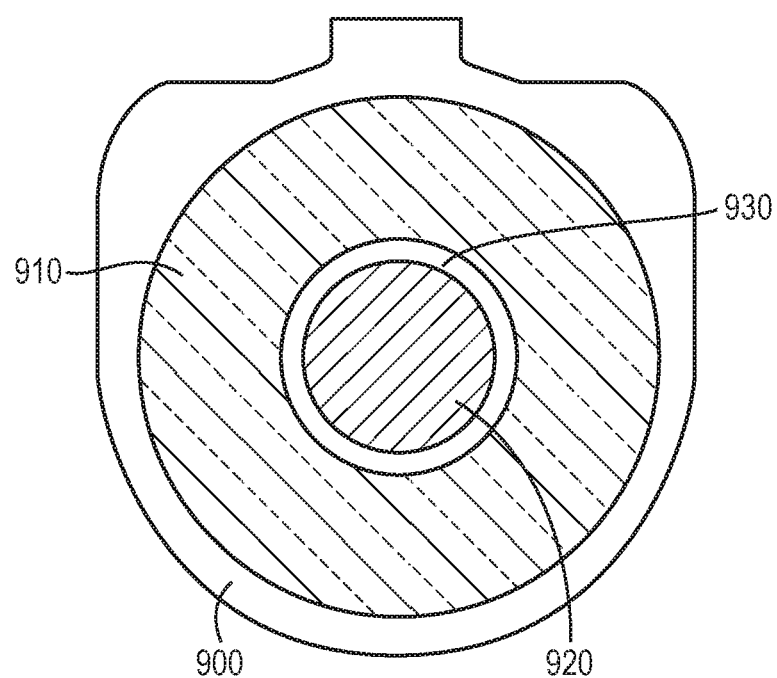
FIG. 9 is a plan view of a portion of an electrolysis chamber incorporating a strain gauge in accordance with various embodiments of the invention.

As shown in FIG. 9, a strain gauge or other pressure-sensing circuitry may be incorporated within or on the bottom surface of pumping chamber 106. For example, the electrolysis electrodes 110 may be disposed on a substrate (or "chip") 900 in an electrode region 910, and the strain gauge 310 or other pressure-sensing circuitry may be disposed in a pressure-sensing region 920 separated from the electrode region 910 by a buffer region 930 (which may be free of electrolysis electrodes and pressure-sensing circuitry). The configuration of FIG. 9 may be more easily manufacturable; since the substrate 900 typically already contains vias and/or other electrical interconnects for supplying power to the electrodes 110, the strain gauge 310 may be easily electrically interconnected using such connections. Specifically, no additional major components may be required to incorporate pressure-sensing region 920 into the pump device 100; that is, only the strain gauge 310 itself, electrical connections thereto, any associated vias, and the pressure-sensing bridge circuit need be incorporated onto substrate 900. The pressure sensitivity of pressure-sensing region 920 may be enhanced in embodiments in which envelope 108 is relatively less flexible.

In various embodiments of the invention, the strain gauge 310 is embedded within or formed on one or more of the components of pump device 100 during the manufacturing thereof. For example, during manufacturing of the tubular component 400 described above, a first polymeric tube (which may include, consist essentially of, or consist of, e.g., parylene) may be deposited or molded. The wire for strain gauge 310 may then be inserted within or wound around the tube, and then a second polymer layer (which may include, consist essentially of, or consist of, e.g., parylene) may be deposited over the wire, thereby embedding the wire within the tubular component 400. The terminal leads of the wire may protrude from the polymer matrix and be electronically connected to the remainder of the strain-gauge circuit and/or other device electronics. Other fabrication techniques usable in accordance with embodiments of the invention include dip coating, etching, vapor deposition, and additive-manufacturing techniques such as three-dimensional printing. Alternatively or in addition, the strain gauge 310 may be attached to a component of pump device 100 via an adhesive (e.g., epoxy) or other fastening means (e.g., one or more clamps).

Drug delivery devices in accordance with embodiments of the invention may undergo a calibration step prior to and/or during implantation. For example, a smart refill system that monitors and stores time and pressure information (e.g., as described in U.S. patent application Ser. No. 14/579,231, filed on Dec. 22, 2014, the entire disclosure of which is incorporated by reference) during various steps (e.g., suction, wash, refill) may be used to monitor and store pressure information for various components of the device to correlate electrical resistance values to pressure values within the device's specific components. Pressure information for various components of the device may be correlated to the pressure values obtained by the smart refill system (e.g., needle tip pressure, reservoir pressure, etc.) to detect any possible occlusions in the fluidic system or the failure of any of the components (e.g., a leak). An error condition may be reported if monitored pressure level deviation exceeds a specific threshold.

Refill steps may also be monitored to ensure proper refilling of the device.

Figure 10A:
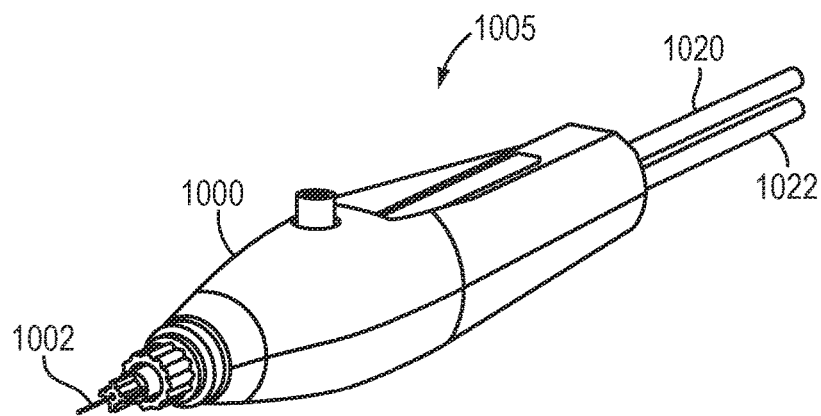
FIG. 10A is a perspective view of a handheld refill tool in accordance with various embodiments of the invention.
Figure 10B:
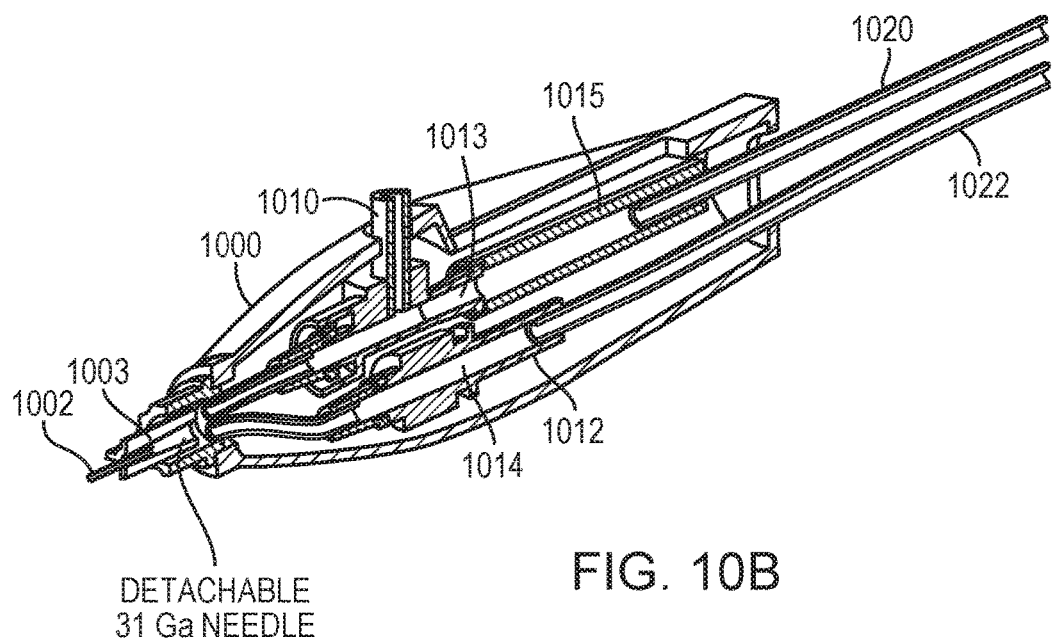
FIG. 10B is a cutaway view of the device shown in FIG. 10A.

With reference to FIGS. 10A and 10B, refill systems usable in accordance with embodiments of the present invention may be implemented in multiple components, one of which is a handpiece 1000. As described in greater detail below, the pumps, control circuitry, and some of the valves and sensors are integrated into a reusable base unit, a pair of fluid channels from which enter the distal end the handpiece 1000; the handpiece terminates in a detachable (and replaceable) refill needle 1002 having a lumen 1003, which is preferably a small-bore needle. The handpiece 1000 includes an ergonomic handle portion 1005 that allows a clinician to refill the implanted device in situ. In various embodiments, the same needle 1002 is used during the entire refill process so as to minimize the needle insertion frequency into the drug reservoir and the associated stress for patient and clinician, as well as the wear on the refill port. A single needle insertion may suffice even if multiple fluids (e.g., multiple separately stored drugs to be administered together) are to be injected into the drug pump device. The needle 1002 may be, thus, sequentially connected to different fluid containers.

The handpiece 1000 is desirably weight-balanced and may have built-in transparent windows so fluid movement can be visually confirmed. For safety purposes, the handpiece 1000 may have a built-in, user-actuated retractable needle-storage slot to conceal and store the needle 1002 when the refill tool is not in use. In certain embodiments, as best seen in the cutaway view of FIG. 10B, the handpiece 1000 may contain a pair of check valves 1010, 1012, two outlet fluid channels 1013, 1014 and a drug reservoir 1015. Either or both check valves 1010, 1012 may be active or passive to help regulate the fluid fill and extraction processes. In the illustrated embodiment, the valve 1010 is a two-way check valve and the valve 1012 is a one-way check valve. The valves 1010, 1012 are fluidically coupled to fluid lines 1020, 1022, respectively. The handpiece 1000 may also contain one or more modalities to assist in detecting the refill port of the device to be refilled. Such modalities may include a pressure sensor, a light source, a capacitive sensing or piezo-element tip, and/or a magnetic or Hall effect structure, which may provide the user with additional feedback throughout the refill process.

Figure 11:
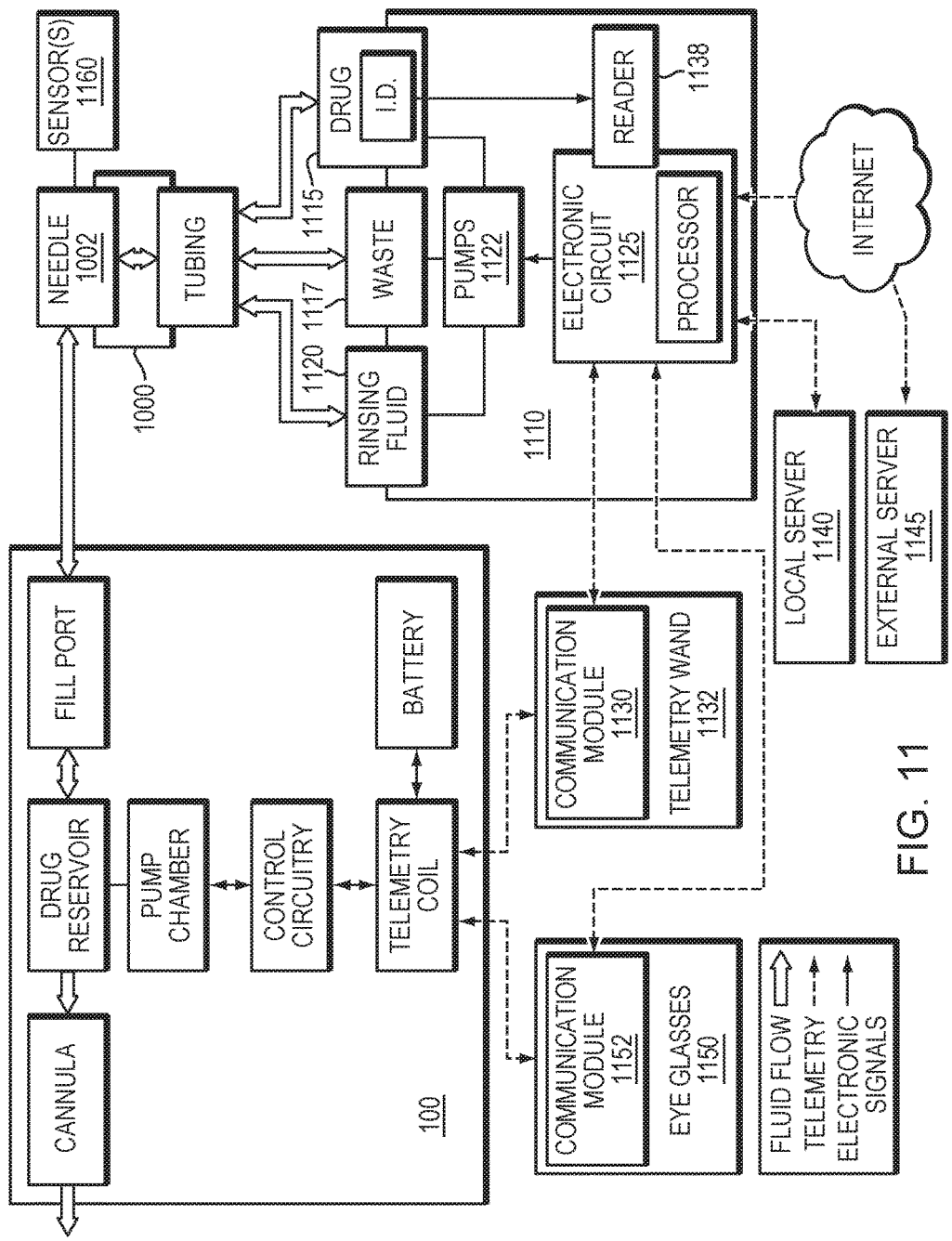
FIG. 11 is a block diagram of a drug pump device and refill system in accordance with various embodiments of the invention, illustrating communication links between various components of the system.

FIG. 11 illustrates the operating environment and general system configuration of a representative refill system usable in embodiments of the present invention. As described herein, the refillable drug-pump device 100 may include a drug reservoir, a pump chamber, and control circuitry for operating the device 100. Drug from the reservoir is delivered to an anatomical site via a cannula, and the reservoir may be refilled by the needle 1002 of the handpiece 1000 via a fill port. Various operative components of the refill system may be housed in a base unit 1110, which contains a drug refill reservoir 1115, a waste reservoir 1117, and a reservoir 1120 for rinsing fluid. A pumping unit 1122 includes one or more pumps, e.g., one or more pneumatic air pumps, vacuum pumps, combination dual-diaphragm pumps, or any other pump configurations known in the field to create a suitable pressure differential. Further, it is well known and common practice in the medical industry to create a sterile barrier between any liquid and the pump itself by using sterile filters and an air gap. This allows the pumping unit 1122 to be modular and reusable. The pumping unit 1122 may include of consist essentially of more than one pump according to the requirements of the refill process such as the number of fluids, fluidic channels, and pump-actuation requirements.

In various embodiments, these pumping units are regulated by software operative within an electronic control circuit 1125 that includes a microprocessor. However, the clinician may opt to manually trigger the start of each phase of the refill procedure using a mechanical actuator after the previous phase has ended. The actuator may be built into the handpiece 1000, but some buttons or switches may be located separately such as in a foot pedal. Since drug-delivery device 100 in accordance with embodiments of the present invention contains one or more strain (i.e., pressure) sensors (and may also include sensors for flow, biologic, etc.), the pumping unit 1122 may actively communicate with the device 100 through telemetry or other electronic communication methods to ensure successful refill and no accidental drug delivery during the refill process. Such communication protocols may also be used during refill to run diagnostic checks on the drug-delivery device. Flow rates and/or pressure readings known to be accurate may be compared to sensor readings from the device 100 to calibrate a flow sensor via a known dosing profile and/or a pressure sensor via sensed pressure fluctuations during the refill process. Such diagnostic and recalibration protocols improve the accuracy of drug delivery over the course of the lifetime of the device 100.

Thus, the control circuitry 1125 of the base unit 1110 may include a communication or telemetry module (including a transceiver and related circuitry) 1130 provided separately from the control circuitry 1125, e.g., in a handheld telemetry wand 1132 that allows the clinician to conveniently bring the wand 1132 in the vicinity of the implanted pump device 100. The wand may be corded to the base unit 1110, or may communicate with the base unit 1110 via a separate wireless connection. If employed, the wand 1132 may be used to interrogate the device 100 and allows for bi-directional data exchange and/or power transfer. Interrogation may involve, for example, switching the device 100 to a refill mode in which the device's internal actuation (electrolysis, electroosmosis, piezo-electric actuation, etc.) is turned off, and information such as refill drug name (e.g., the ID associated with a removable drug reservoir 1115 and read by a reader 1138), concentration, and volume may be transmitted to the device 100. The interrogation step may also include an authentication protocol to prevent drug off-label use and to ensure the implant's software security.

The data exchanged with the drug pump device 100 may be stored on a local server 1140 integrated with or connected to the base unit 1110. Alternatively, the communication module 1130 may permit the base unit 1110 to communicate with an external server 1145, e.g., remotely via the Internet. For example, the base unit 1110 may have Wi-Fi, Zigbee, or a cellular phone chip (GSM, CDMA) that is constantly activated to cellular service or other wireless capability. This permits patient and drug data to be stored outside the refill system ("in the cloud"), and may provide further levels of security and operational flexibility.

In some embodiments, special eyeglasses 1150 equipped with a telemetry module 1152 are used to recharge the battery of the device 100; such eyeglasses are described in U.S. Ser. No. 12/463,251, filed on May 8, 2009, the entire disclosure of which is hereby incorporated by reference. These eyeglasses 1150 and the base unit 1110 of the refill system may be connected to each other or to a common console, and wireless data exchange with the drug pump device 100 may occur via the eyeglasses rather than a separate telemetry wand 1132.

In some embodiments, one or more sensors are placed strategically in the refill system for continuous monitoring and detection of phase completion. In one embodiment, a pressure sensor 1160 in the needle tip 102 may be utilized to detect the pressure in the drug reservoir of the device 100, correlate that pressure to pressures sensed by strain/pressure sensors in the device 100, and/or trigger the initiation and completion of each step of a refill process. The pressure sensor 1160 in combination with passive check valves may be used to fully automate the process. The pressure sensor 1160 in the needle tip 1002 may also detect improper insertion (e.g., midway through a septum) of the refill needle 1002 into the fill port of the device 100. Pressure sensors may be deployed in the drug reservoir 1115 and waste reservoir 1117 to detect possible occlusions in the system, triggering shutdown of the refill process. In some embodiments, a pressure sensor is located within the fluidic path between the pumping unit 1122 and the reservoirs 1115, 1117 to detect faults such as fluidic path leaks.

Flow sensors may be placed inline or around the fluidic paths to monitor the flow of drug refill or waste extraction. In some implementations, these flow sensors are merely structural components such as flexible flaps that have different orientations according to the fluid-flow direction and/or rate. This provides the clinician with a visual verification of flow. In other embodiments, flow sensors utilize time-of-flight, thermal effects, chemical concentration, and/or pressure to provide accurate continuous flow-rate measurements, from which total volumes of wash insertion, wash extraction, and drug refill can be calculated. Other ways of metering fluid volumes delivered and extracted may be used as well.

Implantable devices are vulnerable to tissue ingrowth and possible infection. Accordingly, the refill needle 1002 may contain a biosensor (also indicated at 1160) to detect specific conditions such as inflammatory biomarkers, bacterial infection, etc. Additionally, if the waste reservoir 1117 is separate and removable, additional tests may be performed on the extracted waste fluid using external equipment such as lab assays and a mass spectrometer.

As mentioned above, pressure information monitored (e.g., measured one or more times) within one or more components of the drug pump device 100 may be calibrated based on pressure information monitored within one or more components of the refill system (e.g., needle tip pressure, reservoir pressure, etc.). For example, during a refill step, rinse step, and/or suction (i.e., fluid removal) step, one or more pressure levels (e.g., indicated by measurements of, for example, electrical resistance, from one or more strain sensors) measured within one or more components of the drug pump device 100 may be correlated to one or more pressure levels measured within the refill system. The calibrated pressure information (e.g., one or more of the pressures in the device 100, one or more of the electrical resistance levels of a strain gauge or strain sensor, and/or one or more of the pressures in the refill system) may be stored within memory of the drug pump device 100 (e.g., memory associated with control circuitry 118). The calibrated pressure information may be monitored and/or updated over time to monitor performance of the drug pump device 100 and/or the refill system. Pressures (e.g., indicated by measurements of, for example, electrical resistance, from one or more strain sensors) measured within multiple different components of the drug pump device 100 may also be monitored, compared, calibrated with respect to each other, and/or stored within the memory of the drug pump device 100. An error condition may be reported (via, e.g., an audible and/or visible alert displayed on the drug pump device 100 and/or the refill system) if the monitored and/or calibrated pressure deviates from a predetermined range of operating pressures for the drug pump device 100. For example, the error condition may be triggered if the measured or calibrated pressure falls below a minimum threshold pressure and/or exceeds a maximum threshold pressure.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method of calibrating an implantable drug-delivery device, the method comprising:
   providing a refill apparatus comprising at least one pump, at least one reservoir, an outlet fluid channel fluidically connected to the at least one reservoir, and a needle having a lumen in fluid communication with the outlet fluid channel;
   inserting the needle into a refill port of the implantable drug-delivery device;
   monitoring a pressure level of the outlet fluid channel;
   monitoring a pressure level of at least one component of the implantable drug-delivery device; and
   calibrating the monitored pressure level of the at least one component of the implantable drug-delivery device to the monitored pressure level of the outlet fluid channel.

2. The method of claim 1, further comprising reporting an error condition if at least one of the monitored pressure level of the outlet fluid channel or the monitored pressure level of the at least one component of the implantable drug-delivery device deviates from a predetermined range of pressures.

3. The method of claim 1, further comprising:
   monitoring a pressure level of at least one additional component of the implantable drug-delivery device; and
   calibrating the monitored pressure level of the at least one additional component of the implantable drug-delivery device to the monitored pressure level of the at least one component of the implantable drug-delivery device.

4. The method of claim 1, wherein the at least one component of the implantable drug-delivery device comprises (i) a drug reservoir for containing a therapeutic agent therein and/or (ii) an expandable electrolysis chamber comprising therewithin a plurality of electrolysis electrodes and an electrolysis fluid.

5. The method of claim 4, wherein the drug reservoir comprises at least one flexible membrane.

6. The method of claim 1, wherein at least one of the pressure level of the outlet fluid channel or the pressure level of the at least one component of the implantable drug-delivery device is monitored using a strain gauge.

7. The method of claim 6, wherein at least a portion of the strain gauge comprises an open circuit, the method further comprising triggering the open circuit when the monitored pressure level of the at least one component of the implantable drug-delivery device exceeds or falls below a predetermined threshold pressure.

8. The method of claim 6, wherein at least a portion of the strain gauge comprises two interlocking portions, the method further comprising reversibly separating the two interlocking portions when the monitored pressure level of the at least one component of the implantable drug-delivery device exceeds or falls below a predetermined threshold pressure.

9. The method of claim 6, wherein the strain gauge further comprises data-exchange related circuitry, the method further comprising providing communication, via the data-exchange related circuitry, between the implantable drug delivery device and a base unit associated with the needle.

10. The method of claim 6, further comprising triggering an open circuit within at least a portion of the strain gauge when an error condition is detected.

11. The method of claim 1, further comprising storing the calibrated pressure level of the as least one component of the implantable drug-delivery device within the implantable drug-delivery device.

12. The method of claim 1, further comprising:
    monitoring at least one of a flow of drug refill or a flow of waste extraction; and
    monitoring total volumes of the drug refill, wash insertion, and wash extraction.

13. The method of claim 1, wherein the at least one component of the implantable drug-delivery device comprises (i) a portion of a cannula fluidically coupled to the reservoir and having an exit port outside the implantable drug-delivery device, (ii) a tube fluidically coupled to the cannula, (iii) a check valve fluidically coupled to the cannula, and/or (iv) a portion of the refill port.

* * * * *

UNITED STATES PATENT AND TRADEMARK OFFICE
CERTIFICATE OF CORRECTION

PATENT NO. : 10,307,530 B2
APPLICATION NO. : 14/982246
DATED : June 4, 2019
INVENTOR(S) : Jason Shih and Andrew Dunn Page 1 of 1

It is certified that error appears in the above-identified patent and that said Letters Patent is hereby corrected as shown below:

In the Claims

Claim 11, Column 14, Line 40, "as" should read -- at --

Signed and Sealed this
Twentieth Day of August, 2019

Andrei Iancu
*Director of the United States Patent and Trademark Office*